US008691069B2

(12) United States Patent
Teamey et al.

(10) Patent No.: US 8,691,069 B2
(45) Date of Patent: *Apr. 8, 2014

(54) METHOD AND SYSTEM FOR THE ELECTROCHEMICAL CO-PRODUCTION OF HALOGEN AND CARBON MONOXIDE FOR CARBONYLATED PRODUCTS

(71) Applicant: Liquid Light, Inc., Monmouth Junction, NJ (US)

(72) Inventors: Kyle Teamey, Washington, DC (US); Jerry J. Kaczur, North Miami Beach, FL (US); Robert Page Shirtum, Sonora, TX (US)

(73) Assignee: Liquid Light, Inc., Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/724,996

(22) Filed: Dec. 21, 2012

(65) Prior Publication Data

US 2013/0134049 A1 May 30, 2013

Related U.S. Application Data

(60) Provisional application No. 61/703,232, filed on Sep. 19, 2012, provisional application No. 61/720,670,
(Continued)

(51) Int. Cl.
| | |
|---|---|
| C25B 1/00 | (2006.01) |
| C25C 1/24 | (2006.01) |
| C07C 69/74 | (2006.01) |
| C07C 249/00 | (2006.01) |
| C07C 61/00 | (2006.01) |
| C07C 17/00 | (2006.01) |
| C07C 5/32 | (2006.01) |
| C07C 5/327 | (2006.01) |

(52) U.S. Cl.
USPC .............. 205/555; 205/618; 205/619; 560/1; 560/355; 560/358; 562/400; 570/101; 585/379; 585/654

(58) Field of Classification Search
USPC .............. 560/1, 355, 358; 562/400; 570/101; 585/379, 654; 205/555, 618, 619
See application file for complete search history.

(56) References Cited

U.S. PATENT DOCUMENTS 3,019,256 A * 1/1962 Dunn ........................... 560/206
3,293,292 A 12/1966 Olivier et al.
(Continued)

FOREIGN PATENT DOCUMENTS

CA 1146120 A1 5/1983
CA 1272161 A1 7/1990
(Continued)

OTHER PUBLICATIONS

Mahmood et al., "Use of Gas-Diffusion Electrodes for High-Rate Electrochemical Reduction of Carbon Dioxide. II. Reduction at Metal Phthalocyanine-Impregnated Electrodes", J. of Appl. Electrochem. (no month, 1987), vol. 17, pp. 1223-1227.*

(Continued)

Primary Examiner — Edna Wong
(74) Attorney, Agent, or Firm — Suiter Swantz pc llo (57) ABSTRACT

The present disclosure is a system and method for producing a first product from a first region of an electrochemical cell having a cathode and a second product from a second region of the electrochemical cell having an anode. The method may include a step of contacting the first region with a catholyte including carbon dioxide and contacting the second region with an anolyte including a recycled reactant. The method may further include applying an electrical potential between the anode and the cathode sufficient to produce carbon monoxide recoverable from the first region and a halogen recoverable from the second region.

19 Claims, 6 Drawing Sheets

Related U.S. Application Data filed on Oct. 31, 2012, provisional application No. 61/675,938, filed on Jul. 26, 2012, provisional application No. 61/703,229, filed on Sep. 19, 2012, provisional application No. 61/703,158, filed on Sep. 19, 2012, provisional application No. 61/703,175, filed on Sep. 19, 2012, provisional application No. 61/703,231, filed on Sep. 19, 2012, provisional application No. 61/703,234, filed on Sep. 19, 2012, provisional application No. 61/703,238, filed on Sep. 19, 2012, provisional application No. 61/703,187, filed on Sep. 19, 2012.

(56) References Cited

U.S. PATENT DOCUMENTS

| | | |
|---|---|---|
| 3,326,998 A | 6/1967 | Reusser et al. |
| 3,341,615 A | 9/1967 | Wulf et al. |
| 3,341,616 A | 9/1967 | Vives |
| 3,352,935 A | 11/1967 | Mahan |
| 3,361,653 A | 1/1968 | Miller |
| 3,401,100 A | 9/1968 | Macklin |
| 3,492,209 A | 1/1970 | Miller |
| 3,560,354 A | 2/1971 | Young |
| 3,607,962 A * | 9/1971 | Krekeler et al. ............... 585/325 |
| 3,636,159 A | 1/1972 | Solomon |
| 3,720,591 A | 3/1973 | Skarlos |
| 3,745,180 A | 7/1973 | Rennie |
| 3,764,492 A | 10/1973 | Baizer et al. |
| 3,779,875 A | 12/1973 | Michelet |
| 4,072,583 A | 2/1978 | Hallcher et al. |
| 4,087,470 A | 5/1978 | Suzuki |
| 4,088,682 A | 5/1978 | Jordan |
| 4,162,948 A | 7/1979 | Yagii et al. |
| 4,219,392 A | 8/1980 | Halmann |
| 4,245,114 A | 1/1981 | Peltzman |
| 4,256,550 A | 3/1981 | Niinobe et al. |
| 4,343,690 A | 8/1982 | de Nora |
| 4,381,978 A | 5/1983 | Gratzel et al. |
| 4,450,055 A | 5/1984 | Stafford |
| 4,476,003 A | 10/1984 | Frank et al. |
| 4,523,981 A | 6/1985 | Ang et al. |
| 4,547,271 A | 10/1985 | Bharucha et al. |
| 4,595,465 A | 6/1986 | Ang et al. |
| 4,608,132 A | 8/1986 | Sammells |
| 4,608,133 A | 8/1986 | Morduchowitz et al. |
| 4,619,743 A | 10/1986 | Cook |
| 4,661,422 A | 4/1987 | Marianowski et al. |
| 4,673,473 A | 6/1987 | Ang et al. |
| 4,702,973 A | 10/1987 | Marianowski |
| 4,732,655 A | 3/1988 | Morduchowitz et al. |
| 4,902,828 A | 2/1990 | Wickenhaeuser et al. |
| 4,968,393 A | 11/1990 | Mazur et al. |
| 5,074,974 A | 12/1991 | Toomey, Jr. |
| 5,107,040 A | 4/1992 | Repman et al. |
| 5,155,256 A | 10/1992 | Chapman |
| 5,198,086 A | 3/1993 | Chlanda et al. |
| 5,290,404 A | 3/1994 | Toomey |
| 5,412,150 A | 5/1995 | Wessel |
| 5,443,804 A | 8/1995 | Parker et al. |
| 5,514,492 A | 5/1996 | Marincic et al. |
| 5,654,493 A | 8/1997 | Wessel |
| 5,804,045 A | 9/1998 | Orillon et al. |
| 6,024,935 A | 2/2000 | Mills et al. |
| 6,251,256 B1 | 6/2001 | Blay et al. |
| 6,380,446 B1 | 4/2002 | Drew et al. |
| 6,465,699 B1 | 10/2002 | Grosso |
| 6,777,571 B2 | 8/2004 | Chaturvedi et al. |
| 7,462,752 B2 | 12/2008 | Fong et al. |
| 7,883,610 B2 | 2/2011 | Monzyk et al. |
| 8,313,634 B2 | 11/2012 | Bocarsly et al. |
| 2001/0026884 A1 | 10/2001 | Appleby et al. |
| 2002/0022753 A1 | 2/2002 | Drew et al. |
| 2006/0102468 A1 | 5/2006 | Monzyk et al. |
| 2007/0004023 A1 | 1/2007 | Trachtenberg et al. |
| 2007/0012577 A1 * | 1/2007 | Bulan et al. ............... 205/431 |
| 2007/0224479 A1 | 9/2007 | Tadokoro et al. |
| 2008/0223727 A1 | 9/2008 | Oloman et al. |
| 2008/0248350 A1 | 10/2008 | Little et al. |
| 2008/0283411 A1 | 11/2008 | Eastman et al. |
| 2008/0286643 A1 | 11/2008 | Iwasaki |
| 2008/0296146 A1 | 12/2008 | Toulhoat et al. |
| 2008/0314758 A1 | 12/2008 | Grosso |
| 2009/0014336 A1 | 1/2009 | Olah et al. |
| 2009/0030240 A1 | 1/2009 | Olah et al. |
| 2010/0187123 A1 | 7/2010 | Bocarsly et al. |
| 2010/0187125 A1 | 7/2010 | Sandoval et al. |
| 2010/0191024 A1 | 7/2010 | Uenveren et al. |
| 2010/0196800 A1 | 8/2010 | Markoski et al. |
| 2010/0248042 A1 | 9/2010 | Nakagawa et al. |
| 2010/0270167 A1 | 10/2010 | McFarland |
| 2010/0330435 A1 | 12/2010 | Nemeth et al. |
| 2011/0083968 A1 | 4/2011 | Gilliam et al. |
| 2011/0114501 A1 | 5/2011 | Teamey et al. |
| 2011/0114502 A1 | 5/2011 | Cole et al. |
| 2011/0114503 A1 | 5/2011 | Sivasankar et al. |
| 2011/0114504 A1 | 5/2011 | Sivasankar et al. |
| 2011/0143929 A1 | 6/2011 | Sato et al. |
| 2011/0186441 A1 | 8/2011 | LaFrancois et al. |
| 2011/0226632 A1 | 9/2011 | Cole et al. |
| 2011/0237830 A1 | 9/2011 | Masel |
| 2012/0004448 A1 | 1/2012 | Bhattacharyya et al. |
| 2012/0004449 A1 | 1/2012 | Bhattacharyya |
| 2012/0004454 A1 | 1/2012 | Bhattacharyya et al. |
| 2012/0018311 A1 | 1/2012 | Yotsuhashi et al. |
| 2012/0043301 A1 | 2/2012 | Arvin et al. |
| 2012/0215034 A1 | 8/2012 | McFarland |
| 2012/0228147 A1 | 9/2012 | Sivasankar et al. |
| 2012/0292196 A1 | 11/2012 | Albrecht et al. |
| 2012/0295172 A1 | 11/2012 | Peled et al. |
| 2012/0298522 A1 | 11/2012 | Shipchandler et al. |
| 2012/0329657 A1 | 12/2012 | Eastman et al. |
| 2013/0062216 A1 | 3/2013 | Yotsuhashi et al. |
| 2013/0098772 A1 | 4/2013 | Bocarsly et al. |
| 2013/0105304 A1 | 5/2013 | Kaczur et al. |
| 2013/0105330 A1 | 5/2013 | Teamey et al. |
| 2013/0118511 A1 | 5/2013 | Sivasankar et al. |
| 2013/0134048 A1 * | 5/2013 | Teamey et al. ............... 205/349 |
| 2013/0134049 A1 | 5/2013 | Teamey et al. |
| 2013/0140187 A1 | 6/2013 | Teamey et al. |
| 2013/0180863 A1 | 7/2013 | Kaczur et al. |

FOREIGN PATENT DOCUMENTS

| | | | |
|---|---|---|---|
| CA | 2043256 A1 | 12/1991 | |
| CA | 2391938 A1 | 5/2001 | |
| DE | 1047765 A | 12/1958 | |
| DE | 2301032 A | 7/1974 | |
| FR | 853643 * | 3/1940 | ............... C07C 17/02 |
| GB | 1096847 A | 12/1967 | |
| GB | 1584524 A | 4/1977 | |
| GB | 2038335 A | 7/1980 | |
| GB | 2312218 A | 10/1997 | |
| JP | 64-015388 | 1/1989 | |
| WO | WO 9724320 A1 * | 7/1997 | ............... C07C 263/10 |
| WO | WO 0015586 A1 | 3/2000 | |
| WO | WO0138275 A1 | 5/2001 | |
| WO | WO 200467673 A1 | 8/2004 | |
| WO | 2007041872 A1 | 4/2007 | |
| WO | WO 2007041872 A1 | 4/2007 | |
| WO | WO 2012046362 A1 | 4/2012 | |

OTHER PUBLICATIONS

Tanno et al., "Electrolysis of Iodine Solution in a New Sodium Bicarbonate-Iodine Hybrid Cycle", International Journal of Hydrogen Energy (no month, 1984), vol. 9, No. 10, pp. 841-848. Abstract Only.*

Tanno et al., "Electrolysis of Iodine Solution in a New Sodium Bicarbonate-Iodine Hybrid Cycle", International Journal of Hydrogen Energy (no month, 1984), vol. 9, No. 10, pp. 841-848.*

(56) References Cited

OTHER PUBLICATIONS

Eggins, Brown, McNeill, and Grimshaw, Carbon Dioxide Fixation by Electrochemical Reduction in Water to Oxalate and Glyoxylate, Tetrahedron Letters vol. 29, No. 8, pp. 945-948, 1988, Pergamon Journals Ltd., Printed in Great Britain.
M. Alvarez-Guerra et al., Conversion of carbon dioxide into formate using a continuous electrochemical reduction process in a lead cathode, Chem. Eng. J. (2012), http://dx.doi.org/10.1016/j.cej.2012.06.099.
Satoshi Kaneco, Kenji Iiba, Nobu-Hide Hiei, Kiyohisa Ohta, Takayuki Mizuno, and Tohru Suzuki, Electrochemical reduction of carbon dioxide to ethylene with high Faradaic efficiency at a Cu electrode in CsOH/methanol, Electrochimica Acta 44 (1999) 4701-4706.
Keith Scott, A Preliminary Investigation of the Simultaneous Anodic and Cathodic Production of Glyoxylic Acid, Electrochimica Acta, vol. 36, No. 9, pp. 1447-1452, 1991, Printed in Great Britain.
B. Eneau-Innocent et al., Electroreduction of carbon dioxide at a lead electrode in propylene carbonate: A spectroscopic study, Applied Catalysis B: Environmental 98 (2010) 65-71.
Kotaro Ogura et al., Selective Conversion of CO2 to Ethylene by the Electrolysis at a Three-Phase (Gas/Liquid/Solid) Interface in an Acidic Solution Containing Cupric Ions, Fuel Chemistry Division Preprints 2003, 48(1), 264.
S. Gambino and G. Silvestri, On the electrochemical reduction of carbon dioxide and ethylene, Tetrahedron Letters No. 32, pp. 3025-3028, 1973, Pergamon Press, Printed in Great Britain.
K.S. Udupa, G.S. Subramanian, and H.V.K. Udupa, The electrolytic reduction of carbon dioxide to formic acid, Electrochimica Acta, 1971, vol. 16, pp. 1593 to 1598, Pergamon Press, Printed in Northern Ireland.
Green et al., "Vapor-Liquid Equilibria of Formaldehyde-Methanol-Water", Industrial and Engineering Chemistry (Jan. 1955), vol. 47, No. 1, pp. 103-109.
Shibata et al., "Electrochemical Synthesis of Urea at Gas-Diffusion Electrodes Part VI. Simultaneous Reduction of Carbon Dioxide and Nitrite Ions with Various Metallophthalocyanine Catalysts". J. of Electroanalytical Chemistry (no month, 2001), vol. 507, pp. 177-184.
Jaaskelainen and Haukka, The Use of Carbon Dioxide in Ruthenium Carbonyl Catalyzed 1-hexene Hydroformylation Promoted by Alkali Metal and Alkaline Earth Salts, Applied Catalysis A: General, 247, 95-100 (2003).
Heldebrant et al., "Reversible Zwitterionic Liquids, The Reaction of Alkanol Guanidines, Alkanol Amidines, and Diamines wih CO2", Green Chem. (mo month, 2010), vol. 12, pp. 713-721.
Perez et al., "Activation of Carbon Dioxide by Bicyclic Amidines", J. Org. Chem. (no month, 2004), vol. 69, pp. 8005-8011.
Seshardi G., Lin C., Bocarsly A.B., A new homogeneous electrocatalyst for the reduction of carbon dioxide to methanol at low overpotential, Journal of Electroanalytical Chemistry, 1994, 372, pp. 145-150.
Seshadri et al., A New Homogeneous Electrocatalyst for the Reduction of Carbon Dioxide to Methanol at Low Overpotential, Journal of Electroanalytical Chemistry, 372 (1994), 145-150.
Green et al., Vapor-Liquid Equilibria of Formaldehyde-Methanol-Water, Industrial and Engineering Chemistry (Jan. 1955), vol. 47, No. 1, pp. 103-109.
Scibioh et al., Electrochemical Reduction of Carbon Dioxide: A Status Report, Proc Indian Natn Sci Acad (May 2004), vol. 70, A, No. 3, pp. 407-462.
Gennaro et al., Homogeneous Electron Transfer Catalysis of the Electrochemical Reduction of Carbon Dioxide. Do Aromatic Anion Radicals React in an Outer-Sphere Manner?, J. Am. Chem. Soc. (no month, 1996), vol. 118, pp. 7190-7196.
Perez et al., Activation of Carbon Dioxide by Bicyclic Amidines, J. Org. Chem. (no month, 2004), vol. 69, pp. 8005-8011.
Zaragoza Dorwald, Side Reactions in Organic Synthesis, 2005, Wiley-VCH Verlag GmbH & Co. KGaA, Weinheim, Preface. p. IX.

Liansheng et al, Journal of South Central University Technology, Electrode Selection of Electrolysis with Membrane for Sodium Tungstate Solution, 1999, 6(2), pp. 107-110.
Mahmood et al., Use of Gas-Diffusion Electrodes for High-Rate Electrochemical Reduction of Carbon Dioxide. II. Reduction at Metal Phthalocyanine-Impregnated Electrodes, J. of Appl. Electrochem. (no month, 1987), vol. 17, pp. 1223-1227.
Tanno et al., Electrolysis of Iodine Solution in a New Sodium Bicarbonate-Iodine Hybrid Cycle, International Journal of Hydrogen Energy (no month, 1984), vol. 9, No. 10, pp. 841-848.
Seshadri et al, "A new homogeneous catalyst for the reduction of carbon dioxide to methanol at low overpotential," Journal of Electroanalytical Chemistry, 372 (1994) 145-150.
Hori et al, Chapter on "Electrochemical CO2 Reduction on Metal Electrodes," in the book "Modern Aspects of Electrochemistry," vol. 42, pp. 106 and 107.
Czerwinski et al, "Adsorption Study of CO2 on Reticulated vitreous carbon (RVC) covered with platinum," Analytical Letters, vol. 18, Issue 14 (1985), pp. 1717-1722.
Hammouche et al, Chemical Catalysis of Electrochemical Reactions. Homogeneous Catalysis of the Electrochemical Reduction of Carbon Dioxide by Iron ("0") Porphyrins. Role of the Addition of Magnesium Cations. J. Am. Chem. Soc. 1991, 113, 8455-8466.
Hossain et al., Palladium and Cobalt Complexes of Substituted Quinoline, Bipyridine and Phenanthroline as Catalysts for Electrochemical Reduction of Carbon Dioxide, Electrochimica Acta (no month, 1997), vol. 42, No. 16, pp. 2577-2785.
Scibioh et al., "Electrochemical Reduction of Carbon Dioxide: A Status Report", Proc Indian Natn Sci Acad (May 2004), vol. 70, A, No. 3, pp. 407-462.
Scibioh et al, "Electrochemical Reductin of Carbon Dioxide: A Status Report," Proc. Indian Natn Science Acad., 70, A, No. 3, May 2004, pp. 407-762.
Fukaya et al., "Electrochemical Reduction of Carbon Dioxide to Formate Catalyzed by Rh(bpy)3Cl3", Kagaku Gijutsu Kenkyusho Hokoku (no month, 1986), vol. 81, No. 5, pp. 255-258. 1-page abstract only.
Li et al., "The Electro-Reduction of Carbon Dioxide in a Continuous Reactor", J. of Applied Electrochemistry (no month, 2005), vol. 35, pp. 955-965.
Kaneco et al., "Electrochemical Reduction of Carbon Dioxide to Ethylene with High Faradaic Efficiency at a Cu Electrode in CsOH/Methanol", Electrochimica Acta (no month, 1999), vol. 44, pp. 4701-4706.
Kaneco et al., "Electrochemical Conversion of Carbon Dioxide to Formic Acid on Pb in KOH/Methanol Electrolyte at Ambient Temperature and Pressure", Energy (no month, 1998), vol. 23, No. 12, pp. 1107-1112.
Yuan et al., "Electrochemical Activation of Carbon Dioxide for Synthesis of Dimethyl Carbonate in an Ionic Liquid", Electrochimica Acta (no month, 2009), vol. 54, pp. 2912-2915.
U.S. Appl. No. 13/724,647, filed Dec. 21, 2012; Office Action mailed Oct. 17, 2013.
U.S. Appl. No. 13/787,481, filed Mar. 6, 2013; Office Action mailed Sep. 13, 2013.
U.S. Appl. No. 13/724,082, filed Dec. 21, 2012; Office Action mailed Aug. 12, 2013.
U.S. Appl. No. 13/724,522, filed Dec. 21, 2012; Office Action mailed Oct. 1, 2013.
U.S. Appl. No. 13/724,885, filed Dec. 21, 2012; Office Action mailed Aug. 21, 2013.
U.S. Appl. No. 13/724,231, filed Dec. 21, 2012; Office Action mailed Aug. 20, 2013.
Seshadri et al., "A new homogeneous electrocatalyst for the reduction of carbon dioxide to methanol at low overpotential", Journal of Electroanalytical Chemistry and Interfacial Electro Chemistry, Elsevier, Amsterdam, NL, vol. 372, No. 1-2, Jul. 8, 1994, pp. 145-150.
Hossain et al., "Palladium and cobalt complexes of substituted quinoline, bipyridine and phenanthroline as catalysts for electrochemical reduction of carbon dioxide", Electrochimica Acta, Elsevier Science Publishers, vol. 42, No. 16, Jan. 1, 1997, pp. 2577-2585.

(56) References Cited

OTHER PUBLICATIONS

Fisher et al., "Electrocatalytic reduction of carbon dioxide by using macrocycles of nickel and cobalt", Journal of the American Chemical Society, vol. 102, No. 24, Sep. 1, 1980, pp. 7361-7363.

Ishida et al., Selective Formation of HC00- In the Electrochemical CO2 Reduction Catalyzed by URU(BPY)2(CO)2 3/4 2+ (BPY=2,2'-Bipyridine), Journal of the Chemical Society, Chemical Communications, Chemical Society, Letchworth, GB, Jan. 1, 1987, pp. 131-132.

Zhao et al., "Electrochemical reduction of supercritical carbon dioxide in ionic liquid 1-n-butyl-3-methylimidazolium hexafluorophosphate", Journal of Supercritical Fluids, PRA Press, US, vol. 32, No. 1-3, Dec. 1, 2004, pp. 287-291.

* cited by examiner

FIG. 6

METHOD AND SYSTEM FOR THE ELECTROCHEMICAL CO-PRODUCTION OF HALOGEN AND CARBON MONOXIDE FOR CARBONYLATED PRODUCTS

CROSS-REFERENCE TO RELATED APPLICATIONS

The present application claims the benefit under 35 U.S.C. §119(e) of U.S. Provisional Application Ser. No. 61/720,670 filed Oct. 31, 2012, U.S. Provisional Application Ser. No. 61/703,232 filed Sep. 19, 2012 and U.S. Provisional Application Ser. No. 61/675,938 filed Jul. 26, 2012. Said U.S. Provisional Application Ser. No. 61/720,670 filed Oct. 31, 2012, U.S. Provisional Application Ser. No. 61/703,232 filed Sep. 19, 2012 and U.S. Provisional Application Ser. No. 61/675,938 filed Jul. 26, 2012 are incorporated by reference in their entireties.

The present application also claims the benefit under 35 U.S.C. §119(e) of U.S. Provisional Application Ser. No. 61/703,229 filed Sep. 19, 2012, U.S. Provisional Application Ser. No. 61/703,158 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,234 filed Sep. 19, 2012, U.S. Provisional Application Ser. No. 61/703,238 filed Sep. 19, 2012 and U.S. Provisional Application Ser. No. 61/703,187 filed Sep. 19, 2012. The U.S. Provisional Application Ser. No. 61/703,229 filed Sep. 19, 2012, U.S. Provisional Application Ser. No. 61/703,158 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,234 filed Sep. 19, 2012, U.S. Provisional Application Ser. No. 61/703,238 filed Sep. 19, 2012 and U.S. Provisional Application Ser. No. 61/703,187 filed Sep. 19, 2012 are hereby incorporated by reference in their entireties.

The present application incorporates by reference co-pending U.S. patent application Ser. No. 13/724,339 filed on Dec. 21, 2012, U.S. patent application Ser. No. 13/724,878 filed on Dec. 21, 2012, U.S. patent application Ser. No. 13/724,647 filed on Dec. 21, 2012, U.S. patent application Ser. No. 13/724,231 filed on Dec. 21, 2012, U.S. patent application Ser. No. 13/724,807 filed on Dec. 21, 2012, U.S. patent application Ser. No. 13/724,719 filed on Dec. 21, 2012, U.S. patent application Ser. No. 13/724,082 filed on Dec. 21, 2012, and U.S. patent application Ser. No. 13/724,768 filed on Dec. 21, 2012, now U.S. Pat. No. 8,444,844 in their entireties.

TECHNICAL FIELD

The present disclosure generally relates to the field of electrochemical reactions, and more particularly to methods and/or systems for electrochemical co-production of halogen and carbon monoxide for use in carbonylation reactions.

BACKGROUND

The combustion of fossil fuels in activities such as electricity generation, transportation, and manufacturing produces billions of tons of carbon dioxide annually. Research since the 1970s indicates increasing concentrations of carbon dioxide in the atmosphere may be responsible for altering the Earth's climate, changing the pH of the ocean and other potentially damaging effects. Countries around the world, including the United States, are seeking ways to mitigate emissions of carbon dioxide.

A mechanism for mitigating emissions is to convert carbon dioxide into economically valuable materials such as fuels and industrial chemicals. If the carbon dioxide is converted using energy from renewable sources, both mitigation of carbon dioxide emissions and conversion of renewable energy into a chemical form that can be stored for later use will be possible.

SUMMARY OF THE PREFERRED EMBODIMENTS

The present disclosure is directed to a system and method for producing a first product from a first region of an electrochemical cell having a cathode and a second product from a second region of the electrochemical cell having an anode. The method may include a step of contacting the first region with a catholyte including carbon dioxide and contacting the second region with an anolyte including a recycled reactant. The method may further include applying an electrical potential between the anode and the cathode sufficient to produce carbon monoxide recoverable from the first region and a halogen recoverable from the second region.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the present disclosure may be better understood by those skilled in the art by reference to the accompanying figures in which.

DETAILED DESCRIPTION

Reference will now be made in detail to the subject matter disclosed, which is illustrated in the accompanying drawings.

Referring generally to FIGS. 1-6, systems and methods of electrochemical co-production of products are disclosed. It is contemplated that the electrochemical co-production of products may include a production of a first product, such as reduction of carbon dioxide to carbon monoxide, at a cathode side of an electrochemical cell with co-production of a second product, such as a halogen, at the anode of the electrochemical cell.

Additionally, the present disclosure is directed to a system and method employing an electrochemical cell to produce a first product and a second product as intermediate products in the production of an isocyanate. Advantageously, in one embodiment, system and method employing an electrochemical cell may produce an isocyanate without intermediate formation of phosgene. A method for producing producing a first product from a first region of an electrochemical cell having a cathode and a second product from a second region of the electrochemical cell having an anode may include a step of contacting the first region with a catholyte including carbon dioxide and contacting the second region with an anolyte including a recycled reactant. The method may further include applying an electrical potential between the anode and the cathode sufficient to produce carbon monoxide recoverable from the first region and a halogen recoverable from the second region.

The present disclosure is further directed to production of an additional product, such as isocyanate or alkyl carbonate, via a further reacting the co-products produced via an electrochemical cell, such as carbon monoxide and a halogen, with an additional reactant. It is contemplated that carbon monoxide and halogen may be dried to a level of to less than 0.10 percent water by weight or less. The additional reactant may include at least one of an amine, methyl amine, butyl amine, aniline, diamine, diamino toluene, diamino benzene, 4,4' methylene diphenyl diamine, hexamethylenediamine, meta-tetramethylxylylene diamine, and toluenediamines to form an isocyanate, or at least one of an alcohol, methanol, and ethanol to form a carbonate, and a recycled reactant, such as a hydrogen halide. The recycled reactant may be supplied back to the second region as an input feed. By co-producing products, and avoiding the formation of phosgene, the system and method of present disclosure reduces the danger associated with use of a highly toxic and dangerous chemicals. If phosgene is formed, it may be done on demand and at a scale precisely determined by the size of the electrochemical system, thus mitigating the danger associated with phosgene production. The recycling of a recycled reactant, such as HCl, is also advantageous in that it reduces the energy requirement of the overall process, provides a hydrogen source for $CO_2$ reduction to CO, and precludes the need to dispose of the very strong acid HCl.

In another embodiment of the disclosure, system and method may be employed to produce in the second region of the electrochemical cell, prior to reacting the phosgene with an additional reactant. In another embodiment of the disclosure, system and method may be employed to produce phosgene in the second region of the electrochemical cell. The phosgene produced may be extracted from the second region and the extracted phosgene may be presented through a port for subsequent storage and/or consumption by other devices and/or processes. It is contemplated that the nature of the electrochemical system allows for the production and control of the required amount of phosgene for the reaction to be made without any excess.

Before any embodiments of the disclosure are explained in detail, it is to be understood that the embodiments may not be limited in application per the details of the structure or the function as set forth in the following descriptions or illustrated in the figures. Different embodiments may be capable of being practiced or carried out in various ways. Also, it is to be understood that the phraseology and terminology used herein is for the purpose of description and should not be regarded as limiting. The use of terms such as "including," "comprising," or "having" and variations thereof herein are generally meant to encompass the item listed thereafter and equivalents thereof as well as additional items. Further, unless otherwise noted, technical terms may be used according to conventional usage. It is further contemplated that like reference numbers may describe similar components and the equivalents thereof.

Figure 1:
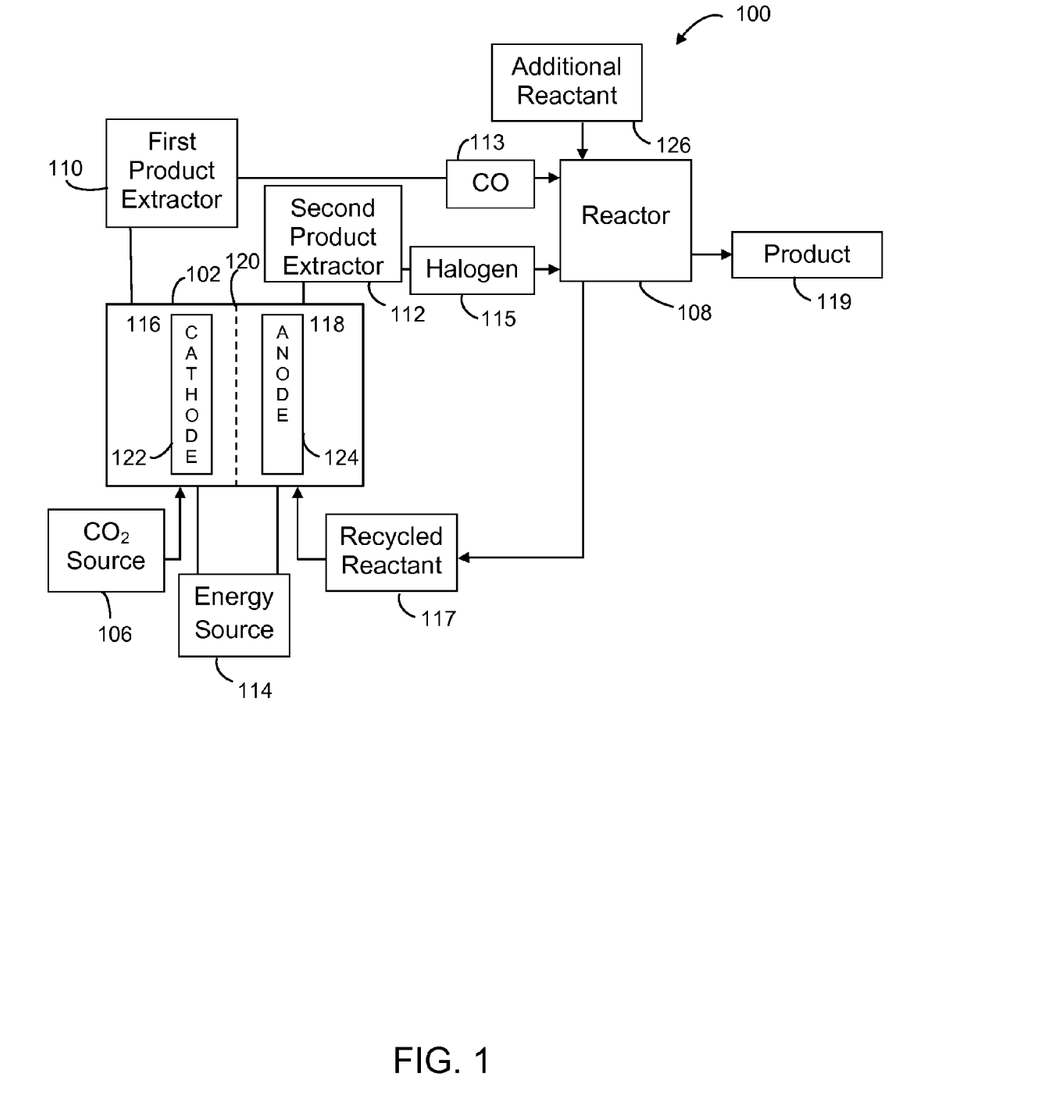
FIG. 1 is a block diagram of a system in accordance with an embodiment of the present disclosure.

Referring to FIG. 1, a block diagram of a system 100 in accordance with an embodiment of the present disclosure is shown. System (or apparatus) 100 generally includes an electrochemical cell (also referred as a container, electrolyzer, or cell) 102, a carbon dioxide source 106, a reactor 108, a first product extractor 110 and a first product such as carbon monoxide 113, a second product extractor 112, a second product such as a halogen 115, and an energy source 114.

Electrochemical cell 102 may be implemented as a divided cell. The divided cell may be a divided electrochemical cell and/or a divided photoelectrochemical cell. Electrochemical cell 102 may include a first region 116 and a second region 118. First region 116 and second region 118 may refer to a compartment, section, or generally enclosed space, and the like without departing from the scope and intent of the present disclosure. First region 116 may include a cathode 122. Second region 118 may include an anode 124. First region 116 may include a catholyte, the catholyte including carbon dioxide which may be dissolved in the catholyte. Second region 118 may include an anolyte which may include a recycled reactant. Energy source 114 may generate an electrical potential between the anode 124 and the cathode 122. The electrical potential may be a DC voltage. Energy source 114 may be configured to supply a variable voltage or constant current to electrochemical cell 102. Separator 120 may selectively control a flow of ions between the first region 116 and the second region 118. Separator 120 may include an ion conducting membrane or diaphragm material.

Electrochemical cell 102 is generally operational to reduce carbon dioxide in the first region 116 to a first product, such as carbon monoxide 113 recoverable from the first region 116 while producing a second product, such as a halogen 115 recoverable from the second region 118. Carbon dioxide source 106 may provide carbon dioxide to the first region 116 of electrochemical cell 102. In some embodiments, the carbon dioxide is introduced directly into the region 116 containing the cathode 122. It is contemplated that carbon dioxide source 106 may include a source of a mixture of gases in which carbon dioxide has been filtered from the gas mixture.

First product extractor 110 may implement an organic product and/or inorganic product extractor. First product extractor 110 is generally operational to extract (separate) the first product, such as carbon monoxide 113, from the first region 116. The extracted carbon monoxide may be presented through a port of the system 100 for subsequent storage and/or consumption by other devices and/or processes.

The anode side of the reaction occurring in the second region 118 may include a recycled reactant 117 supplied to the second region 118. The second product recoverable from the second region 118 may be a halogen 115. Recycled reactant 117 may include a hydrogen halide, such as HCl, or a halide salt that may be a byproduct of reactor 108. For example, the recycled reactant may include AX where A is H, Li, Na, K, Cs, Mg, Ca, or other metal, or $R_4P^+$, $R_4N^+$—where each R is independently alkyl or aryl—or a cation; and X is F, Cl, Br, I, or an anion; and mixtures thereof. Examples are in the table below.

TABLE 1

| Chemical Feed to Anode | Oxidation Product(s) |
|---|---|
| Halides ($F^-$, $Cl^-$, $Br^-$, $I^-$) | Halogens ($F_2$, $Cl_2$, $Br_2$, $I_2$) |
| Hydrogen halides (HF, HCl, HBr, HI) | Halogens ($F_2$, $Cl_2$, $Br_2$, $I_2$) |

Second product extractor 112 may extract the second product, such as a halogen 115 from the second region 118. The extracted second product may be presented through a port of the system 100 for subsequent storage and/or consumption by other devices and/or processes. It is contemplated that first product extractor 110 and/or second product extractor 112 may be implemented with electrochemical cell 102, or may be remotely located from the electrochemical cell 102. Additionally, it is contemplated that first product extractor 110 and/or second product extractor 112 may be implemented in a variety of mechanisms and to provide desired separation methods, such as fractional distillation or molecular sieve drying, without departing from the scope and intent of the present disclosure.

Carbon monoxide 113 and halogen 115 may be presented to another reactor, such as a reactor 108, along with an additional reactant 126. It is contemplated that carbon monoxide 113 and halogen 115 may be dried to a level of 0.10 percent by weight of water, preferably less than 0.01 percent weight of water (100 ppm by weight) or less water content in both the carbon monoxide and halogen gases to improve the reaction yield at reactor 108. Additional reactant 126 may include amine, methyl amine, butyl amine, aniline, diamine, diamino toluene, diamino benzene, 4,4' methylene diphenyl diamino, hexamethylenediamine, meta-tetramethylxylylene diamine, and toluenediamines, or at least one of an alcohol, methanol, and ethanol, and mixtures thereof. Reactor 108 may produce byproducts, such as a recycled reactant 117 and product 119. Product 119 may be dependent upon the type of additional reactant 126 and may include isocyanate, methyl isocyanate, butyl isocyanate, phenyl isocyanate, diisocyanate, methylene-diphenylisocyanate, phenyl-diisocyanate, hexamethylene-diisocyanate, toluene-diisocyanate, meta-tetramethylxylylene-diisocyanate, alkyl carbonate, dimethyl carbonate, ethylmethyl carbonate or diethyl carbonate.

Recycled reactant 117 may be recycled back to the second region 118 as an input feed to the second region 118 of electrochemical cell 102. Recycled reactant 117 may be recycled back to the second region 118 of electrochemical cell 102 as either a pure anhydrous gas or in the liquid phase. The gas phase may be generally preferred in order to minimize energy requirements. Chlorine or a similar halogen is thereby recycled, while carbon monoxide 113 is produced at the first region 116 from $CO_2$. The use of $CO_2$ as a feed for making carbon monoxide is advantageous in that $CO_2$ is safe to store and handle and does not require the large steam reforming infrastructure normally needed to make carbon monoxide from natural gas.

It is contemplated that an additional source of recycled reactant may be further supplied as an input feed to the second region 118 of the electrochemical cell 102 without departing from the scope and intent of the present disclosure.

Through the co-production of a first product and a second product, such as carbon monoxide 113 and halogen 115, the overall energy requirement for making each of the first product and second product may be reduced by 50% or more. In addition, electrochemical cell 102 may be capable of simultaneously producing two or more products with high selectivity.

The oxidation of the recycled reactant, such as hydrogen halides, produces protons and electrons that are utilized to reduce carbon dioxide. Reactions occurring at the cathode will generally take place in a solvent which may include water, methanol, acetonitrile, propylene carbonate, ionic liquids, or other solvents in which $CO_2$ is soluble. It may also occur in the gas phase as long as water vapor is present in the gas stream. An anode reaction may occur in gas phase, for instance in the case of gas phase reactant such as a hydrogen halide. The anode reaction may also occur in liquid phase, such as the case of a hydrogen halide in solution.

In a preferred embodiment, isocyanates such as methylene diphenyl diisocyanate (MDI) or toluene diisocyanate (TDI) may be produced, with the recycled reactant 117 byproduct of HCl from formation of the isocyanate recycled back to the second region 118 of the electrochemical cell 102 where it may be utilized again in the evolution of carbon monoxide and $Cl_2$. Separation steps may be utilized to dry the carbon monoxide gas stream and to separate unreacted HCl from $Cl_2$.

As one embodiment of a recycled reactant 117, HCl may be a feed going into the second region 118 of the electrochemical cell 102. Recycled reactant 117 may be circulated with a pump in an anolyte circulation loop where HCl is converted to $Cl_2$ as a gas or liquid and $H^+$ ions may cross the separator 120 into the first region 116.

On the cathode side, carbon dioxide may be reacted on a high surface area cathode to produce, in this example, carbon monoxide. A circulation pump may be used to provide mass transfer to obtain a high Faradaic efficiency conversion to carbon monoxide.

Electrochemical cell 102 may be operated at a current density of >3 $kA/m^2$ (300 $mA/cm^2$), or in suitable range of 0.5 to 5 $kA/m^2$ or higher if needed. The current density of the formation of chlorine from HCl may be operated at even higher current densities. Electrochemical cell 102 may be liquid phase in both the first region 116 and second region 118, or in the preferred embodiment, may be liquid phase in the first region 116 and with a gas phase second region 118 wherein gas phase HCl is fed directly to the anolyte of the second region 118.

The operating voltage of the electrochemical cell 102 at a current density of 1 $kA/m^2$ is estimated to be somewhere between 1.0-2.5 volts, because the half cell voltage of an anolyte reaction is expected to be between 0.6V and 1.2V. In comparison, the comparable cell voltage using a 1 M sulfuric acid anolyte with the formation of oxygen operating at 1 $kA/m^2$ will likely be between 2.0V and 4V.

In the case of a liquid anolyte, the HCl anolyte concentration may be in the range of 5 wt % to 50 wt %, more preferably in the range of 10 wt % to 40 wt %, and more preferably in the 15 wt % to 30 wt % range, with a corresponding 2 to 30 wt % chlorine content in the solution phase. The HCl content in the anolyte solution may affect the anolyte solution conductivity, and thus the second region 118 IR voltage drop. If the anode is run with gas phase HCl, then HCl concentrations may approach 100% by wt % and be run in anhydrous conditions.

The anode preferably has a polymeric bound carbon current distributor anode and may use a carbon felt with a specific surface area of 50 $cm^2/cm^3$ or more that fills a gap between the cathode backplate and the membrane, thus having a zero gap anode. The carbon felt may also be electrically and physically bonded to the carbon current distributor anode by a carbon conductive bonding agent. Metal and/or metal oxide catalysts may be added to the anode in order to decrease anode potential and/or to increase the operating anode current density. An example is the use of a $RuO_2$ catalyst.

The cathode may be a number of high surface area materials to include copper and copper alloys, bronze and its alloys, stainless steels, carbon, and silicon, which may be further coated with a layer of material which may be a conductive metal or semiconductor. A very thin plastic screen against the cathode side of the membrane may be employed to prevent the membrane from touching the high surface area cathode structure. The high surface area cathode structure is mechanically pressed against the cathode current distributor backplate, which may be composed of material that has the same surface composition as the high surface area cathode.

Faradaic current efficiency of the anode is preferably between 90 to 100%, and the acetate Faradaic current efficiency is preferably between 25 and 100%. The flow circulation of the anolyte and catholyte is such that it provides sufficient flow for the reactions.

Figure 2:
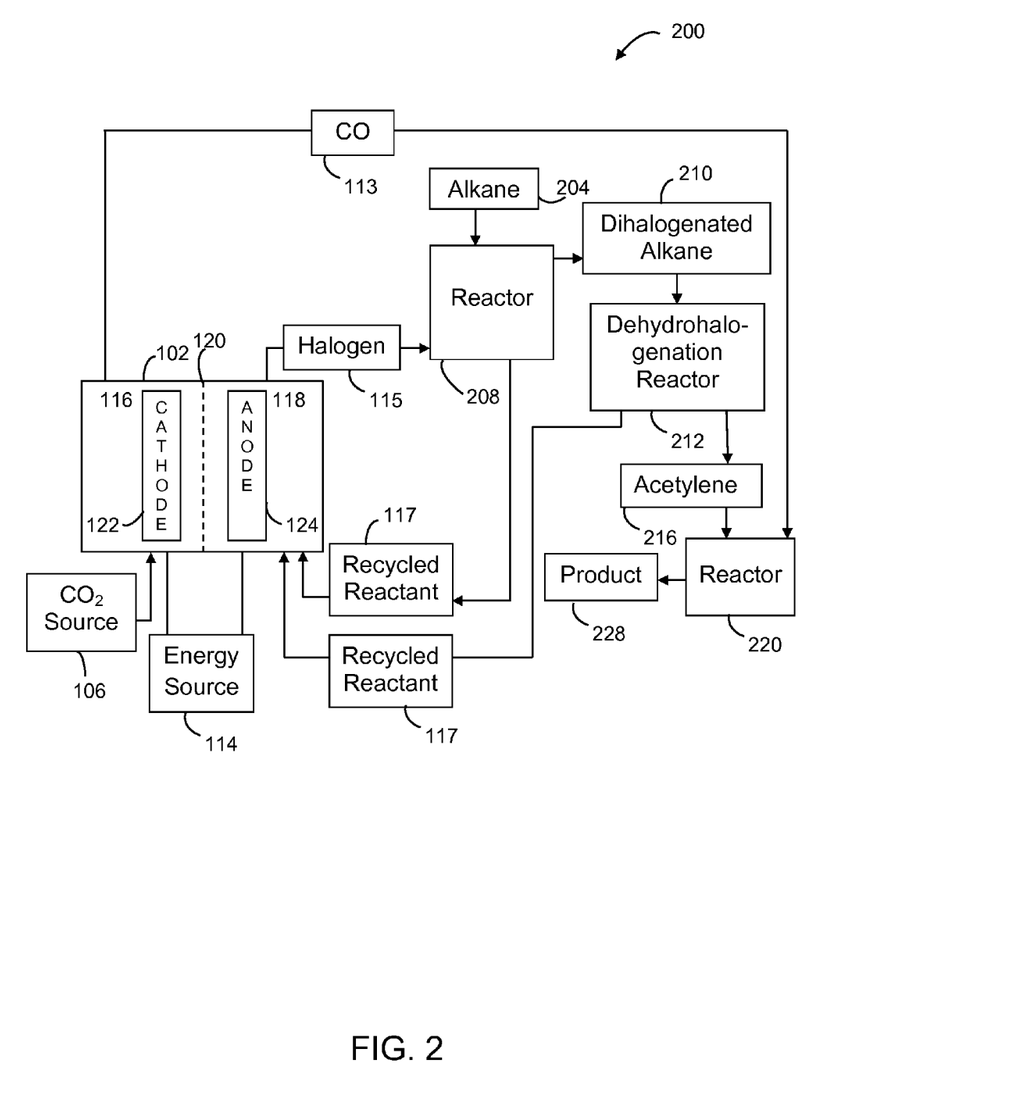
FIG. 2 is a block diagram of a system in accordance with another embodiment of the present disclosure.

Referring to FIG. 2, a block diagram of a system in accordance with another embodiment of the present disclosure is shown. System 200 may include electrochemical cell 102 may operate for co-production of a first product and second product, such as carbon monoxide 113 and halogen 115 as intermediate products employed for production of a product 228, such as an acrylic acid or acrylic acid esters. In an advantageous aspect of the disclosure, acrylic acid or acrylic acid esters may be produced using a phosgene-free electrochemical process. Additionally, precursors needed for acrylic acid or acrylic acid esters may be co-produced from the electrochemical cell 102.

Halogen 115 may be presented to another reactor, such as a reactor 208, along with an additional reactant, such as an alkane 204. Alkane 204 may be ethane. Reactor 208 may produce byproducts, such as a recycled reactant 117 and a dihalogenated alkane 210, such as a dihalogenated ethane. Recycled reactant 117, such as HCl may be recycled back to the second region 118 as an input feed to the second region 118 of electrochemical cell 102. Dihalogenated alkane 210 may be presented to dehydrohalogenation reactor 212. Dehydrohalogenation reactor 212 may conduct a dehydrohalogenation reaction to produce products which may include additional recycled reactant 117 and acetylene 216. Additional recycled reactant 117, such as HCl, may be recycled back to the second region 118 as an input feed to the second region 118 of electrochemical cell 102.

Acetylene 216 may be reacted with carbon monoxide 113 co-produced with water and/or alcohol from carbon dioxide at the first region at reactor 220. Reactor 220 may produce a product 228. Product 228 may include an acrylic acid or acrylic acid esters.

Figure 3:
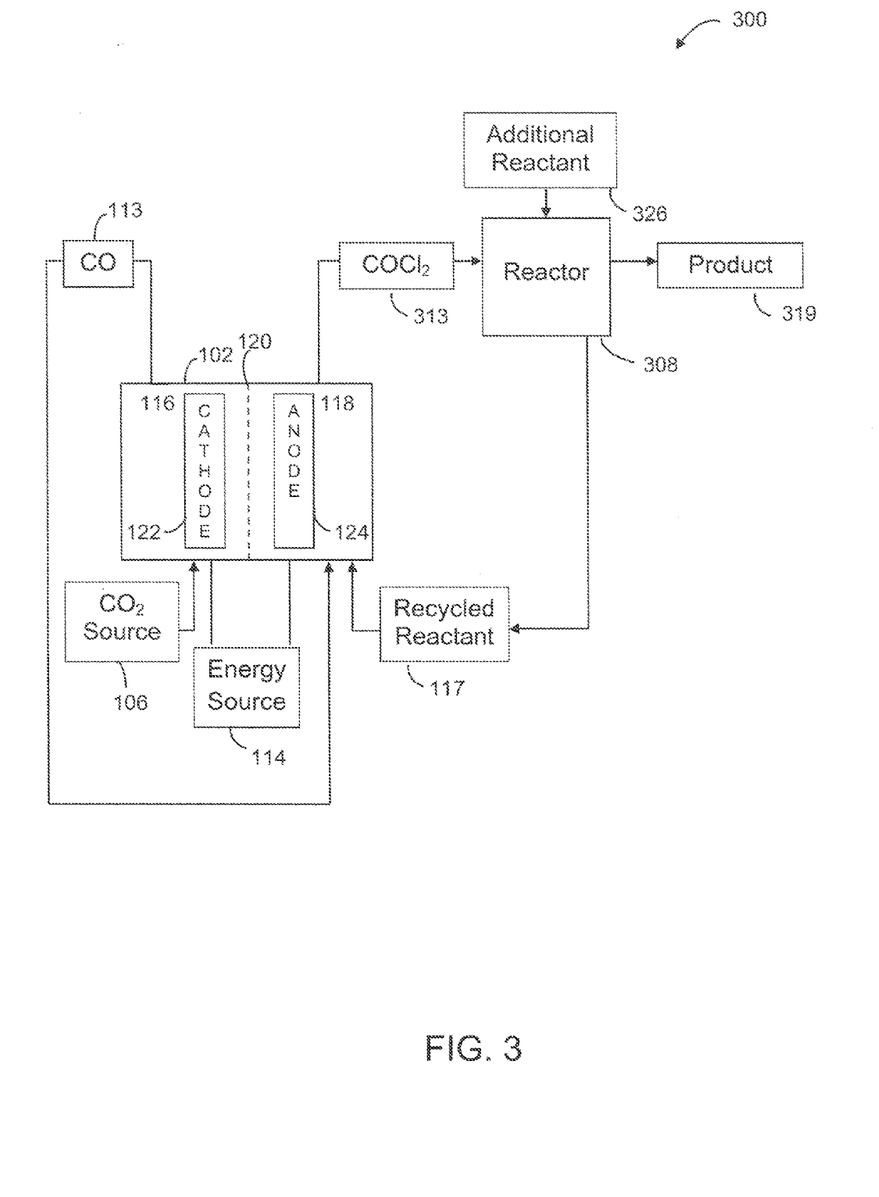
FIG. 3 is a block diagram of a system in accordance with an additional embodiment of the present disclosure.

Referring to FIG. 3, a block diagram of a system 300 in accordance with an additional embodiment of the present disclosure is shown. In an alternative embodiment for production of a product, such as isocyanate or alkyl carbonate, phosgene may be produced entirely within the electrochemical cell 102. System 300 may include electrochemical cell 102 which may operate for co-production of a first product and second product, such as carbon monoxide 113 and phosgene 313 as intermediate products employed for production of a product 319. Carbon monoxide 113 may be supplied as an additional input feed to second region 118.

Phosgene 313 may react with an additional reactant 326 at reactor 308 to produce byproducts of a recycled reactant 117 and product 319. Recycled reactant 117, such as HCl, may be recycled back to the second region 118 as an input feed to the second region 118 of electrochemical cell 102. Additional reactant 326 may include an amine, methyl amine, butyl amine, aniline, diamine, diamino toluene, diamino benzene, 4,4' methylene diphenyl diamine, hexamethylenediamine, meta-tetramethylxylylene diamine, and toluenediamines, or at least one of an alcohol, methanol, and ethanol, and mixtures thereof. Product 319 may be dependent upon the type of additional reactant 326 and may include isocyanate, methyl isocyanate, butyl isocyanate, phenyl isocyanate, diisocyanate, methylene-diphenylisocyanate, phenyl-diisocyanate, hexamethylene-diisocyanate, toluene-diisocyanate, meta-tetramethylxylylene-diisocyanate, alkyl carbonate, dimethyl carbonate, ethylmethyl carbonate or diethyl carbonate.

In one embodiment, carbon monoxide 113 may be dried and fed into the second region 118 with recycled reactant 117, such as anhydrous HCl. The anhydrous HCl and carbon monoxide may react in the second region to form phosgene 313.

Figure 4:
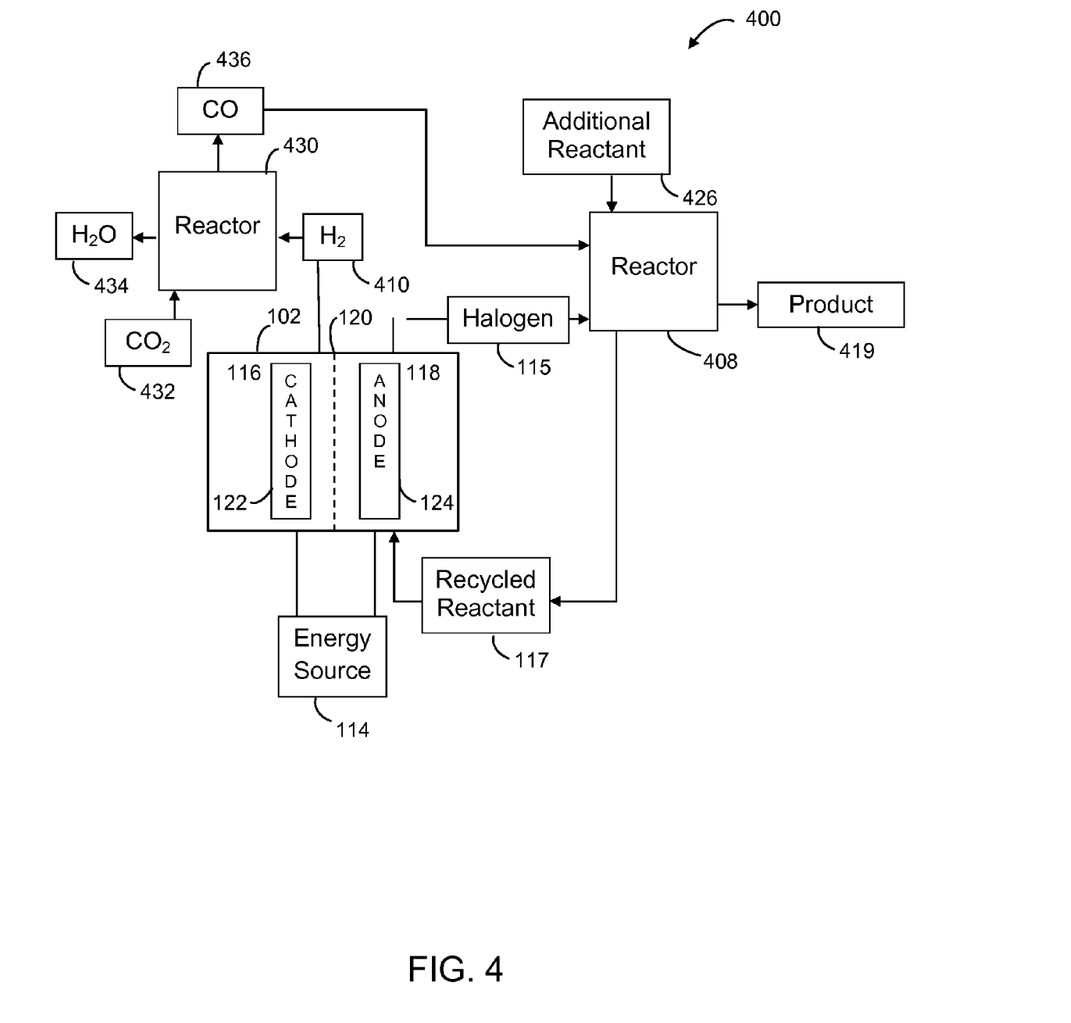
FIG. 4 is a block diagram of a system in accordance with another additional embodiment of the present disclosure.
Figure 5:
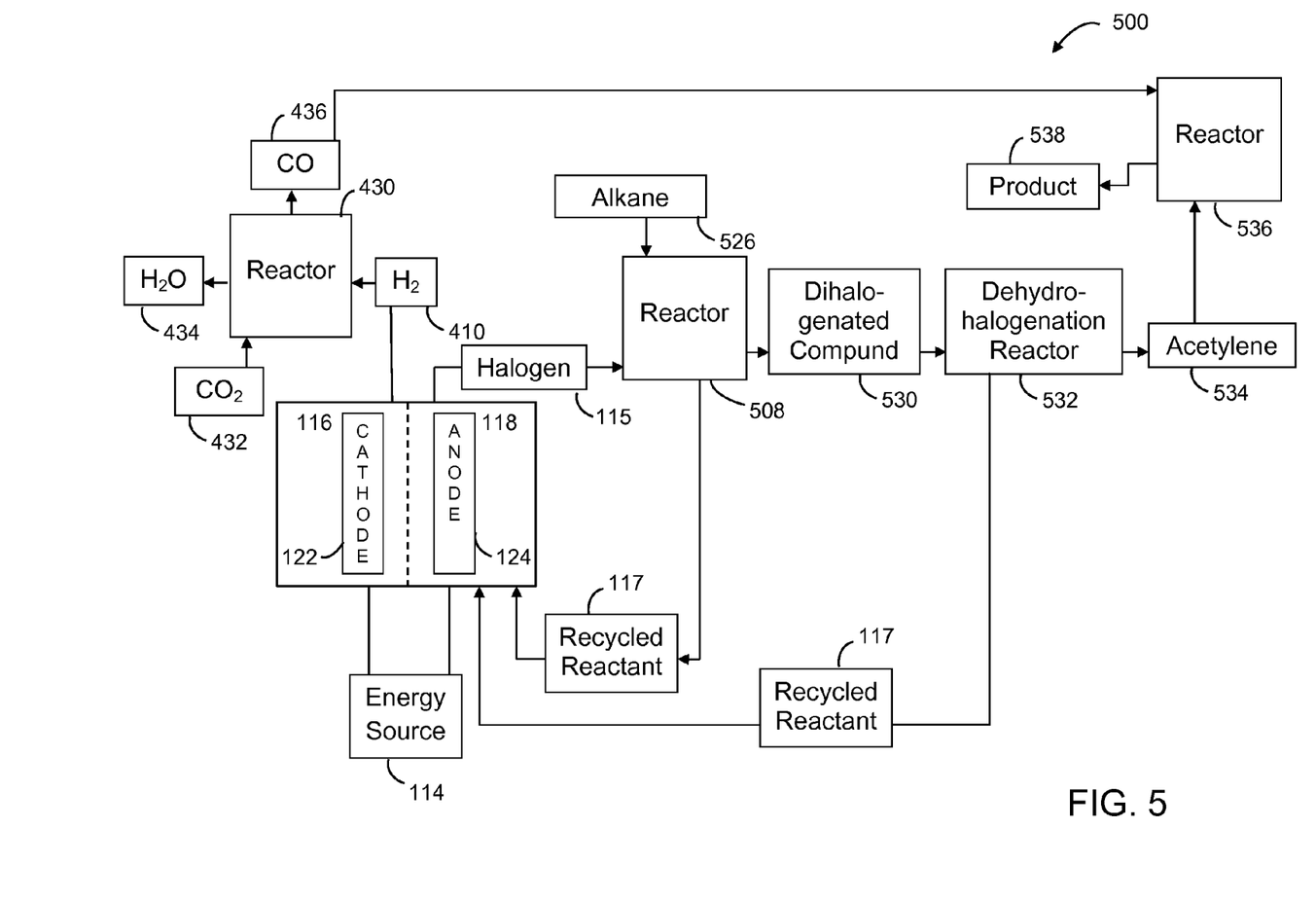
FIG. 5 is a block diagram of a system in accordance with another additional embodiment of the present disclosure.
Figure 6:
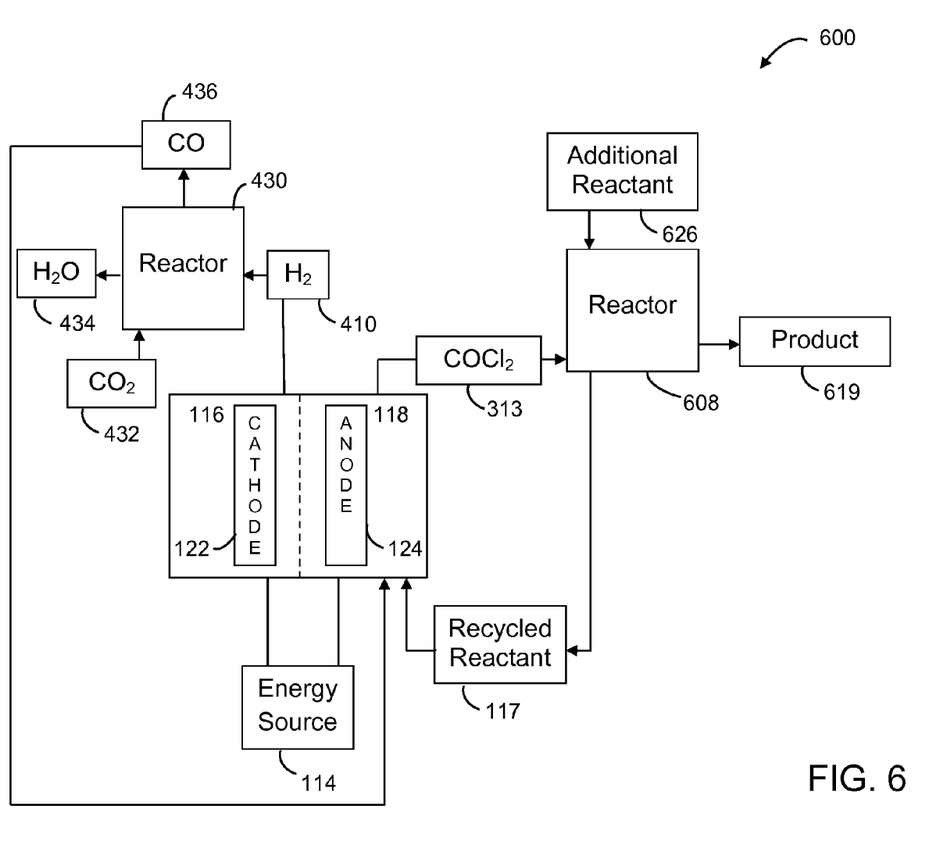
FIG. 6 is a a block diagram of a system in accordance with another additional embodiment of the present disclosure.

Referring to FIGS. 4-6, block diagrams of systems 400, 500 and 600 show alternative embodiments of systems 100, 200 and 300 of FIGS. 1-3, respectively. Referring specifically to FIG. 4, first region 116 of electrochemical cell 102 may produce a first product of $H_2$ 410 which is combined with carbon dioxide 432 in a reactor 430 which may perform a reverse water gas shift reaction. This reverse water gas shift reaction performed by reactor 430 may produce water 434 and carbon monoxide 436. Carbon monoxide 436 may be fed to reactor 438.

Second region 118 may co-produce a halogen 115 that is supplied to reactor 408. It is contemplated that carbon monoxide 113 and halogen 115 may be dried to a level of 0.10 percent by weight of water, preferably less than 0.01 percent weight of water (100 ppm by weight) or less water content in both the carbon monoxide and halogen gases to improve the reaction at reactor 408. Reactor 408 may react carbon monoxide 113, halogen 115 and additional reactant 426. Additional reactant 126 may include amine, methyl amine, butyl amine, aniline, diamine, di amino toluene, diamino benzene, 4,4' methylene diphenyl diamine, hexamethylenediamine, meta-tetramethylxylylene diamine, and toluenediamines, or at least one of an alcohol, methanol, and ethanol, and mixtures thereof. Reactor 408 may produce byproducts, such as a recycled reactant 117 and product 419. Product 419 may be dependent upon the type of additional reactant 426 and may include isocyanate, methyl isocyanate, butyl isocyanate, phenyl isocyanate, diisocyanate, methylene-diphenylisocyanate, phenyl-diisocyanate, hexamethylene-diisocyanate, toluene-diisocyanate, meta-tetramethylxylylene-diisocyanate, alkyl carbonate, dimethyl carbonate, ethylmethyl carbonate or diethyl carbonate.

Referring specifically to FIG. 5, first region 116 of electrochemical cell 102 may produce a first product of $H_2$ 410 which is combined with carbon dioxide 432 in a reactor 430 which may perform a reverse water gas shift reaction. This reverse water gas shift reaction performed by reactor 430 may produce water 434 and carbon monoxide 436. Carbon monoxide 436 may be fed to reactor 536.

Second region 118 of electrochemical cell 102 may co-produce a halogen 115 that is supplied to reactor 408. Halogen 115 may be presented to reactor 508, along with an additional reactant, such as an alkane 526. Alkane 526 may be ethane. Reactor 508 may produce byproducts, such as a recycled reactant 117 and a dihalogenated alkane 530, such as a dihalogenated ethane. Recycled reactant 117, such as HCl may be recycled back to the second region 118 as an input feed to the second region 118 of electrochemical cell 102. Dihalogenated alkane 530 may be presented to dehydrohalogenation reactor 532. Dehydrohalogenation reactor 532 may perform a dehydrohalogenation reaction to produce products which may include additional recycled reactant 117 and acetylene 534. Additional recycled reactant 117, such as HCl, may be recycled back to the second region 118 as an input feed to the second region 118 of electrochemical cell 102.

Acetylene 534 may be reacted with carbon monoxide 113 produced via the reverse water gas shift reaction of reactor 430. Reactor 536 may produce a product 538. Product 538 may include acrylic acid or acrylic acid esters.

Referring specifically to FIG. 6, first region 116 of electrochemical cell 102 may produce a first product of $H_2$ 410 which is combined with carbon dioxide 432 in a reactor 430 which may perform a reverse water gas shift reaction. This reverse water gas shift reaction performed by reactor 430 may produce water 434 and carbon monoxide 436. Carbon monoxide 436 may be supplied to the second region 118 of electrochemical cell 102.

Second region 118 of electrochemical cell 102 may co-produce phosgene 313. Phosgene may react with an additional reactant 626 at reactor 608 to produce byproducts of a recycled reactant 117 and product 619. Recycled reactant 117, such as HCl, may be recycled back to the second region 118 as an input feed to the second region 118 of electrochemical cell 102. Additional reactant 626 may include amine, methyl amine, butyl amine, aniline, diamine, diamino toluene, diamino benzene, 4,4' methylene diphenyl diamine, hexamethylenediamine, meta-tetramethylxylylene diamine, and toluenediamines, or at least one of an alcohol, methanol, and ethanol, and mixtures thereof. Product 619 may be dependent upon the type of additional reactant 626 and may include isocyanate, methyl isocyanate, butyl isocyanate, phenyl isocyanate, diisocyanate, methylene-diphenylisocyanate, phenyl-diisocyanate, hexamethylene-diisocyanate, toluene-diisocyanate, meta-tetramethylxylylene-diisocyanate, alkyl carbonate, dimethyl carbonate, ethylmethyl carbonate or diethyl carbonate.

It is contemplated that a receiving a feed may include various mechanisms for receiving a supply of a product, whether in a continuous, near continuous or batch portions.

It is further contemplated that the structure and operation of the electrochemical cell 102 may be adjusted to provide desired results. For example, the electrochemical cell 102 may operate at higher pressures, such as pressure above atmospheric pressure which may increase current efficiency and allow operation of the electrochemical cell at higher current densities.

Additionally, the cathode 122 and anode 124 may include a high surface area electrode structure with a void volume which may range from 30% to 98%. The electrode void volume percentage may refer to the percentage of empty space that the electrode is not occupying in the total volume space of the electrode. The advantage in using a high void volume electrode is that the structure has a lower pressure drop for liquid flow through the structure. The specific surface area of the electrode base structure may be from 2 $cm^2/cm^3$ to 500 $cm^2/cm^3$ or higher. The electrode specific surface area is a ratio of the base electrode structure surface area divided by the total physical volume of the entire electrode. It is contemplated that surface areas also may be defined as a total area of the electrode base substrate in comparison to the projected geometric area of the current distributor/conductor back plate, with a preferred range of 2× to 1000× or more. The actual total active surface area of the electrode structure is a function of the properties of the electrode catalyst deposited on the physical electrode structure which may be 2 to 1000 times higher in surface area than the physical electrode base structure.

Cathode 122 may be selected from a number of high surface area materials to include copper and copper alloys, stainless steels, transition metals and their alloys, carbon, and silicon, which may be further coated with a layer of material which may be a conductive metal or semiconductor. The base structure of cathode 122 may be in the form of fibrous, reticulated, or sintered powder materials made from metals, carbon, or other conductive materials including polymers. The materials may be a very thin plastic screen incorporated against the cathode side of the membrane 120 from directly touching the high surface area cathode structure. The high surface area cathode structure may be mechanically pressed against a cathode current distributor backplate, which may be composed of material that has the same surface composition as the high surface area cathode.

In addition, cathode 122 may be a suitable conductive electrode, such as Al, Au, Ag, Bi, C, Cd, Co, Cr, Cu, Cu alloys (e.g., brass and bronze), Ga, Hg, In, Mo, Nb, Ni, $NiCo_2O_4$, Ni alloys (e.g., Ni 625, NiHX), Ni—Fe alloys, Pb, Pd alloys (e.g., PdAg), Pt, Pt alloys (e.g., PtRh), Rh, Sn, Sn alloys (e.g., SnAg, SnPb, SnSb), Ti, V, W, Zn, stainless steel (SS) (e.g., SS 2205, SS 304, SS 316, SS 321), austenitic steel, ferritic steel, duplex steel, martensitic steel, Nichrome (e.g., NiCr 60:16 (with Fe)), elgiloy (e.g., Co—Ni—Cr), degenerately doped p-Si, degenerately doped p-Si:As, degenerately doped p-Si:B, degenerately doped n-Si, degenerately doped n-Si:As, and degenerately doped n-Si:B. Other conductive electrodes may be implemented to meet the criteria of a particular application. For photoelectrochemical reductions, cathode 122 may be a p-type semiconductor electrode, such as p-GaAs, p-GaP, p-InN, p-InP, p-CdTe, p-GaInP$_2$ and p-Si, or an n-type semiconductor, such as n-GaAs, n-GaP, n-InN, n-InP, n-CdTe, n-GaInP$_2$ and n-Si. Other semiconductor electrodes may be implemented to meet the criteria of a particular application including, but not limited to, CoS, $MoS_2$, TiB, $WS_2$, SnS, $Ag_2S$, $CoP_2$, $Fe_3P$, $Mn_3P_2$, MoP, $Ni_2Si$, $MoSi_2$, WSi2, $CoSi_2$, $Ti_4O_7$, $SnO_2$, GaAs, GaSb, Ge, and CdSe.

Catholyte may include a pH range from 1 to 12, preferably from pH 4 to pH 10. The selected operating pH may be a function of any catalysts utilized in operation of the electrochemical cell 102. Preferably, catholyte and catalysts may be selected to prevent corrosion at the electrochemical cell 102. Catholyte may include homogeneous catalysts. Homogeneous catalysts are defined as aromatic heterocyclic amines and may include, but are not limited to, unsubstituted and substituted pyridines and imidazoles. Substituted pyridines and imidazoles may include, but are not limited to mono and disubstituted pyridines and imidazoles. For example, suitable catalysts may include straight chain or branched chain lower alkyl (e.g., Cl—C10) mono and disubstituted compounds such as 2-methylpyridine, 4-tertbutyl pyridine, 2,6 dimethylpyridine (2,6-lutidine); bipyridines, such as 4,4'-bipyridine; amino-substituted pyridines, such as 4-dimethylamino pyridine; and hydroxyl-substituted pyridines (e.g., 4-hydroxypyridine) and substituted or unsubstituted quinoline or isoquinolines. The catalysts may also suitably include substituted or unsubstituted dinitrogen heterocyclic amines, such as pyrazine, pyridazine and pyrimidine. Other catalysts generally include azoles, imidazoles, indoles, oxazoles, thiazoles, substituted species and complex multi-ring amines such as adenine, pterin, pteridine, benzimidazole, phenonthroline and the like.

The catholyte may include an electrolyte. Catholyte electrolytes may include alkali metal bicarbonates, carbonates, sulfates, phosphates, borates, and hydroxides. The electrolyte may comprise one or more of $Na_2SO_4$, KCl, $NaNO_3$, NaCl, NaF, $NaClO_4$, $KClO_4$, $K_2SiO_3$, $CaCl_2$, a guanidinium cation, a H cation, an alkali metal cation, an ammonium cation, an alkylammonium cation, a tetraalkyl ammonium cation, a halide anion, an alkyl amine, a borate, a carbonate, a guanidinium derivative, a nitrite, a nitrate, a phosphate, a polyphosphate, a perchlorate, a silicate, a sulfate, and a hydroxide. In one embodiment, bromide salts such as NaBr or KBr may be preferred.

The catholyte may further include an aqueous or non-aqueous solvent. An aqueous solvent may include greater than 5% water. A non-aqueous solvent may include as much as 5% water. A solvent may contain one or more of water, a protic solvent, or an aprotic polar solvent. Representative solvents include methanol, ethanol, acetonitrile, propylene carbonate, ethylene carbonate, dimethyl carbonate, diethyl carbonate, dimethylsulfoxide, dimethylformamide, acetonitrile, acetone, tetrahydrofuran, N,N-dimethylacetamide, dimethoxyethane, diethylene glycol dimethyl ester, butyronitrile, 1,2-difluorobenzene, γ-butyrolactone, N-methyl-2-pyrrolidone, sulfolane, 1,4-dioxane, nitrobenzene, nitromethane, acetic anhydride, ionic liquids, and mixtures thereof.

In one embodiment, a catholyte/anolyte flow rate may include a catholyte/anolyte cross sectional area flow rate range such as 2-3,000 gpm/ft$^2$ or more (0.0076-11.36 m$^3$/m$^2$). A flow velocity range may be 0.002 to 20 ft/sec (0.0006 to 6.1 m/sec). Operation of the electrochemical cell catholyte at a higher operating pressure allows more dissolved carbon dioxide to dissolve in the aqueous solution. Typically, electrochemical cells can operate at pressures up to about 20 to 30 psig in multi-cell stack designs, although with modifications, the electrochemical cells may operate at up to 100 psig. The electrochemical cell may operate anolyte at the same pressure range to minimize the pressure differential on a separator 120 or membrane separating the two regions. Special electrochemical designs may be employed to operate electrochemical units at higher operating pressures up to about 60 to 100 atmospheres or greater, which is in the liquid $CO_2$ and supercritical $CO_2$ operating range.

In another embodiment, a portion of a catholyte recycle stream may be separately pressurized using a flow restriction with backpressure or using a pump, with $CO_2$ injection, such that the pressurized stream is then injected into the catholyte region of the electrochemical cell which may increase the amount of dissolved $CO_2$ in the aqueous solution to improve the conversion yield. In addition, microbubble generation of carbon dioxide can be conducted by various means in the catholyte recycle stream to maximize carbon dioxide solubility in the solution.

Catholyte may be operated at a temperature range of −10 to 95° C., more preferably 5-60° C. The lower temperature will be limited by the catholytes used and their freezing points. In general, the lower the temperature, the higher the solubility of $CO_2$ in an aqueous solution phase of the catholyte, which would help in obtaining higher conversion and current efficiencies. The drawback is that the operating electrochemical cell voltages may be higher, so there is an optimization that would be done to produce the chemicals at the lowest operating cost. In addition, the catholyte may require cooling, so an external heat exchanger may be employed, flowing a portion, or all, of the catholyte through the heat exchanger and using cooling water to remove the heat and control the catholyte temperature.

Anolyte operating temperatures may be in the same ranges as the ranges for the catholyte, and may be in a range of 0° C. to 95° C. In addition, the anolyte may require cooling, so an external heat exchanger may be employed, flowing a portion, or all, of the anolyte through the heat exchanger and using cooling water to remove the heat and control the anolyte temperature.

Electrochemical cells may include various types of designs. These designs may include zero gap designs with a finite or zero gap between the electrodes and membrane, flow-by and flow-through designs with a recirculating catholyte electrolyte utilizing various high surface area cathode materials. The electrochemical cell may include flooded co-current and counter-current packed and trickle bed designs with the various high surface area cathode materials. Also, bipolar stack cell designs and high pressure cell designs may also be employed for the electrochemical cells.

Anode electrodes may be the same as cathode electrodes or different. Anode 124 may include electrocatalytic coatings applied to the surfaces of the base anode structure. Anolytes may be the same as catholytes or different. Anolyte electrolytes may be the same as catholyte electrolytes or different. Anolyte may comprise solvent. Anolyte solvent may be the same as catholyte solvent or different. For example, for HBr, acid anolytes, and oxidizing water generating oxygen, the preferred electrocatalytic coatings may include precious metal oxides such as ruthenium and iridium oxides, as well as palladium, platinum and gold and their combinations as metals and oxides on valve metal substrates such as titanium, tantalum, zirconium, or niobium. For bromine and iodine anode chemistry, carbon and graphite are particularly suitable for use as anodes. Polymeric bonded carbon material may also be used. For other anolytes, comprising alkaline or hydroxide electrolytes, anodes may include carbon, cobalt oxides, stainless steels, transition metals, and their alloys and combinations. High surface area anode structures that may be used which would help promote the reactions at the anode surfaces. The high surface area anode base material may be in a reticulated form composed of fibers, sintered powder, metallic foams, sintered screens, and the like, and may be sintered, welded, or mechanically connected to a current distributor back plate that is commonly used in bipolar cell assemblies. In addition, the high surface area reticulated anode structure may also contain areas where additional applied catalysts on and near the electrocatalytic active surfaces of the anode surface structure to enhance and promote reactions that may occur in the bulk solution away from the anode surface such as the reaction between bromine and the carbon based reactant being introduced into the anolyte. The anode structure may be gradated, so that the density of the may vary in the vertical or horizontal direction to allow the easier escape of gases from the anode structure. In this gradation, there may be a distribution of particles of materials mixed in the anode structure that may contain catalysts, such as metal halide or metal oxide catalysts such as iron halides, zinc halides, aluminum halides, cobalt halides, for reactions between bromine and a carbon-based reactant. For other anolytes comprising alkaline, or hydroxide electrolytes, anodes may include carbon, cobalt oxides, stainless steels, and their alloys and combinations.

Separator 120, also referred to as a membrane, between a first region 116 and second region 118, may include cation ion exchange type membranes. Cation ion exchange membranes which have a high rejection efficiency to anions may be preferred. Examples of such cation ion exchange membranes may include perfluorinated sulfonic acid based ion exchange membranes such as DuPont Nafion® brand unreinforced types N117 and N120 series, more preferred PTFE fiber reinforced N324 and N424 types, and similar related membranes manufactured by Japanese companies under the supplier trade names such as AGC Engineering (Asahi Glass) under their trade name Flemion®. Other multi-layer perfluorinated ion exchange membranes used in the chlor alkali industry may have a bilayer construction of a sulfonic acid based membrane layer bonded to a carboxylic acid based membrane layer, which efficiently operates with an anolyte and catholyte above a pH of about 2 or higher. These membranes may have a higher anion rejection efficiency. These are sold by DuPont under their Nafion® trademark as the N900 series, such as the N90209, N966, N982, and the 2000 series, such as the N2010, N2020, and N2030 and all of their types and subtypes. Hydrocarbon based membranes, which are made from of various cation ion exchange materials can also be used if the anion rejection is not as desirable, such as those sold by Sybron under their trade name Ionac®, Engineering (Asahi Glass) under their trade name AGC Engineering (Asahi Glass) under their Selemion® trade name, and Tokuyama Soda, among others on the market. Ceramic based membranes may also be employed, including those that are called under the general name of NASICON (for sodium super-ionic conductors) which are chemically stable over a wide pH range for various chemicals and selectively transports sodium ions, the composition is $Na_{1+x}Zr_2Si_xP_3-xO_{12}$, and well as other ceramic based conductive membranes based on titanium oxides, zirconium oxides and yttrium oxides, and beta aluminum oxides. Alternative membranes that may be used are those with different structural backbones such as polyphosphazene and sulfonated polyphosphazene membranes in addition to crown ether based membranes. Preferably, the membrane or separator is chemically resistant to the anolyte and catholyte and operates at temperatures of less than 600 degrees C., and more preferably less than 500 degrees C.

A rate of the generation of reactant formed in the anolyte compartment from the anode reaction, such as the oxidation of HCl to chlorine, is contemplated to be proportional to the applied current to the electrochemical cell 102. The rate of the input or feed of the carbon-based reactant, for example CO, into the anolyte region 118 should then be fed in proportion to the generated reactant. The molar ratio of the carbon-based reactant to the generated anode reactant may be in the range of 100:1 to 1:10, and more preferably in the range of 50:1 to 1:5. The anolyte product output in this range can be such that the output stream contains little or no free chlorine in the product output to the second product extractor 112, or it may contain unreacted chlorine. The operation of the extractor 112 and its selected separation method, for example fractional distillation, the actual products produced, and the selectivity of the wanted reaction would determine the optimum molar ratio of the carbon-based reactant to the generated reactant in the anode compartment. Any of the unreacted components would be recycled to the second region 118.

Similarly, a rate of the generation of the formed electrochemical carbon dioxide reduction product, such as carbon monoxide, is contemplated to be proportional to the applied current to the electrochemical cell 102. The rate of the input or feed of the carbon dioxide source 106 into the first region 116 should be fed in a proportion to the applied current. The cathode reaction efficiency would determine the maximum theoretical formation in moles of the carbon dioxide reduction product. It is contemplated that the ratio of carbon dioxide feed to the theoretical moles of potentially formed carbon dioxide reduction product would be in a range of 100:1 to 2:1, and preferably in the range of 50:1 to 5:1, where the carbon dioxide is in excess of the theoretical required for the cathode reaction. The carbon dioxide excess would then be separated in the extractor 110 and recycled back to the first region 116.

In the present disclosure, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A method for co-producing carbon monoxide from a first region of an electrochemical cell having a cathode and a halogen from a second region of the electrochemical cell having an anode, the method comprising the steps of:
   contacting the first region of the electrochemical cell with a catholyte comprising carbon dioxide;
   contacting the second region of the electrochemical cell with an anolyte comprising a recycled reactant, wherein the recycled reactant is HX, where X is selected from the group consisting of F, Cl, Br, and I; and
   applying an electrical potential between the anode and the cathode of the electrochemical cell sufficient to reduce the carbon dioxide and co-produce the carbon monoxide recoverable from the first region of the electrochemical cell and the halogen recoverable from the second region of the electrochemical cell.

2. The method according to claim 1, wherein the halogen includes at least one of $F_2$, $Cl_2$, $Br_2$ or $I_2$.

3. The method according to claim 1, further comprising:
   drying the carbon monoxide recovered from the first region and the halogen recovered from the second region to less than 0.10 percent water by weight.

4. The method according to claim 3, further comprising:
   reacting the carbon monoxide recovered from the first region, the halogen recovered from the second region and an additional reactant to form a third product and the recycled reactant.

5. The method according to claim 4, wherein the additional reactant includes at least one of an amine, methyl amine, butyl amine, aniline, a diamine, di amino toluene, diamino benzene, 4,4'-methylene diphenyl diamine, hexamethylenediamine, meta-tetramethylxylylene-diamine, and toluenediamines, or at least one of an alcohol, methanol, and ethanol, and mixtures thereof.

6. The method according to claim 4, wherein the third product includes one of isocyanate, methyl isocyanate, butyl isocyanate, phenyl isocyanate, diisocyanate, methylenediphenylisocyanate, phenyl-diisocyanate, hexamethylene-diisocyanate, toluene-diisocyanate, meta-tetramethylxylylene-diisocyanate, alkyl carbonate, dimethyl carbonate, ethylmethyl carbonate or diethyl carbonate.

7. The method according to claim 1, further comprising:
   reacting the halogen recovered from the second region and an additional reactant to form a third product and the recycled reactant.

8. The method according to claim 7, wherein the additional reactant is a halocarbon and the third product is a dihalogenated hydrocarbon.

9. The method according to claim 8, further comprising:
   converting the dihalogenated hydrocarbon to acetylene and the recycled reactant via a dehydrohalogenation reaction.

10. The method according to claim 9, further comprising:
    reacting the carbon monoxide recovered from the first region, acetylene, and one of water or alcohol to form one of acrylic acid or acrylic acid esters.

11. The method according to claim 1, wherein the cathode and the anode are separated by an ion permeable barrier that operates at a temperature less than 600 degrees C.

12. The method according to claim 11, wherein the ion permeable barrier includes one of a polymeric or inorganic ceramic-based ion permeable barrier.

13. The method according to claim 1, wherein the catholyte is liquid phase and the anolyte is gas phase.

14. The method according to claim 13, wherein the liquid phase of the catholyte liquid phase is an aqueous solution including an electrolyte including one or more of alkali metal sulfates, carbonates, chlorides, phosphates, borates, nitrates, and nitrites.

15. The method of claim 13, wherein the catholyte further includes an aqueous solvent which is more than 5% by weight water.

16. The method of claim 13, wherein the catholyte further includes a non-aqueous solvent which is less than 5% by weight water.

17. The method of claim 13, where the catholyte further includes at least one of water, a protic solvent, or an aprotic solvent.

18. The method of claim 1, wherein the catholyte further includes a homogeneous catalyst.

19. The method of claim 18, wherein the homogeneous catalyst includes at least one of unsubstituted pyrimindine, substituted pyridine, imidazole, dinitrogen heterocyclic amine, azole, imidazole, indole, oxazole or thiazole.

* * * * *